United States Patent [19]

Becker

[11] 4,262,143
[45] Apr. 14, 1981

[54] PREPARATION OF HYDROPEROXIDES

[75] Inventor: Mitchell Becker, Teaneck, N.J.

[73] Assignee: Halcon International, Inc., New York, N.Y.

[21] Appl. No.: 12,639

[22] Filed: Feb. 16, 1979

Related U.S. Application Data

[63] Continuation of Ser. No. 594,837, Jul. 10, 1975, abandoned.

[51] Int. Cl.$^3$ .................. C07C 179/04; C07D 301/19
[52] U.S. Cl. ............................. 568/574; 260/348.29; 260/348.12
[58] Field of Search ............ 568/569, 570, 573, 574; 260/348.12, 348.29

[56] References Cited

U.S. PATENT DOCUMENTS

| | | | |
|---|---|---|---|
| 2,680,139 | 6/1954 | Fenoglio et al. | 568/570 |
| 2,681,937 | 6/1954 | Mosnier et al. | 568/574 |
| 2,715,646 | 8/1955 | Hawkins et al. | 568/573 |
| 3,350,422 | 10/1967 | Kollar | 568/570 |
| 3,439,001 | 4/1969 | Pell | 260/348.29 |
| 3,459,810 | 8/1969 | Choo et al. | 568/569 |
| 3,475,498 | 10/1969 | Choo | 568/569 |
| 3,647,886 | 3/1972 | Mead | 568/570 |
| 3,839,461 | 10/1974 | Aoshima et al. | 568/574 |
| 3,933,921 | 1/1976 | Suda et al. | 568/569 |

FOREIGN PATENT DOCUMENTS

| | | | |
|---|---|---|---|
| 510517 | 3/1955 | Canada | 568/574 |
| 1228033 | 4/1971 | United Kingdom | 568/570 |

*Primary Examiner*—Werren B. Lone
*Attorney, Agent, or Firm*—William C. Long; David Dick; Riggs T. Stewart

[57] ABSTRACT

In the preparation of ethylbenzene hydroperoxide by reacting ethylbenzene with molecular oxygen, selectivity and reaction rate are improved by incorporating in the oxidation mixture a small amount of a hydroxide or salt of sodium or potassium.

16 Claims, No Drawings

PREPARATION OF HYDROPEROXIDES

This is a continuation of application Ser. No. 594,837 filed July 10, 1975, now abandoned.

This invention relates to the preparation of ethylbenzenehydroperoxide by reacting ethylbenzene with molecular oxygen.

The preparation of hydroperoxides by reacting appropriate hydrocarbons with molecular oxygen is a well-known reaction which is extensively discussed, for example, in "Organic Peroxides" by E. G. E. Hawkins (D. Van Nostrand Company, Inc., 1961) and in "Organic Peroxides" (3 vols.) edited by Daniel Swern (Wiley-Interscience, 1970, 1971 and 1972). A particularly important application of this reaction from a commerical standpoint is the preparation of hydroperoxides which are used for the epoxidation of olefins, especially alkenes such as propylene, to form oxirane compounds, such as propylene oxide. For this purpose the tertiary alkanes, such as isobutane, and the aralkanes, especially ethylbenzene and cumene, as well as the cycloalkanes, such as cyclohexane, are particularly suitable as hydrocarbon feeds. Epoxidation reactions of this type, which are generally carried out in the presence of appropriate catalysts are described, for example, in Kollar U.S. Pat. Nos. 3,350,422 and 3,351,635, which are incorporated herein by reference. In a typical commercial plant, the preparation of the hydroperoxide and the reaction of the hydroperoxide with the olefin to produce the desired oxirane compound are all part of an integrated system in which various components of the reaction mixtures are circulated or recycled for reuse. This is particularly true of the hydrocarbon which is supplied to the oxidation reaction in which the hydroperoxide is formed. In a typical operation, only a portion of the hydrocarbon is converted to the hydroperoxide. As a result, unreacted hydrocarbon is present in the system and, for obvious economic reasons, it must be eventually returned, along with fresh make-up hydrocarbon, to the feed to the oxidation zone.

The oxidation reaction has been found, however, to be particularly sensitive to the presence of contaminants in the recycle hydrocarbon although the exact nature of these contaminants is not entirely known. It has been observed that such contaminants can have a marked adverse effect upon the selectivity of the oxidation reaction in favor of the desired hydroperoxides, as well as upon the rate of reaction. Moreover, the problem of insuring adequate rate and sufficient selectivity is particularly serious in the case of secondary hydrocarbons, i.e., hydrocarbons having a secondary carbon atom, such as ethylbenzene, and in the case of cycloalkanes, such as cyclohexane, since the corresponding hydroperoxide tends to be less stable than the hydroperoxides formed from tertiary hydrocarbons, i.e., hydrocarbons having a tertiary carbon atom, such as cumene.

Thus, it is well known that in the normal course of an oxidation reaction of this type using only fresh hydrocarbon, selectivity tends to decrease as conversion increases under normal operation, i.e., as more of the hydrocarbon is reacted and the concentration of the hydroperoxide in the reaction mixture is increased. There is, therefore, a normal relationship between these two factors. When, however, recycle hydrocarbon containing contaminants is used, the selectivity deviates from this norm and is consistently lower for a given conversion and the deviation becomes even greater at increased conversions. If, for example, the normal selectivity using fresh ethylbenzene as the sole hydrocarbon feed for the preparation of ethylbenzene hydroperoxide at 8 weight percent hydroperoxide concentration is 90.5% and the normal selectivity at 15 weight percent hydroperoxide concentration is 83%, it has been observed that when the feed is changed to nine parts of recycle hydrocarbon per part of fresh hydrocarbon, the selectivity at 8 weight % hydroperoxide concentration declines to 86.7%, i.e., a decrease of 3.8 percentage points from the norm, and the selectivity at 15 weight % concentration declines to 73%, i.e., a decrease of 10 percentage points from the norm. Clearly, the adverse effect of contaminants becomes more pronounced as conversion increases and the practical disadvantages are apparent.

The term "conversion" as used herein designates the ratio, expressed on a molar basis, of $$\frac{\text{moles hydrocarbon reacting}}{\text{moles hydrocarbon fed}} \times 100,$$

and the term "selectivity" designates the ratio, expressed on a molar basis, of $$\frac{\text{moles hydroperoxide formed}}{\text{moles hydrocarbon reacting}} \times 100.$$

Thus, the problems of reaction rate and selectivity arise not only as a result of the use of the recycle hydrocarbon but they are especially aggravated when an oxidation plant is operated at or close to capacity, i.e., when increased quantities of molecular oxygen are passed through the hydrocarbon and conversion is increased. It has been observed that such capacity operation leads to drastically reduced selectivity in favor of the desired hydroperoxide, as pointed out above and increased production of the by-products of the reaction, predominantly alcohols and ketones. In the case of the production of ethylbenzene hydroperoxide, these by-products include alphamethylbenzyl alcohol and acetophenone. There is also observed a significant decrease in reaction rate.

Various techniques for promoting the oxidation of hydrocarbons in favor of the production of hydroperoxides have been proposed and many of these proposals have involved the addition to the oxidation system of substantial quantities of additives which have been variously characterized as "catalysts" or "inhibitors" or "promoters" or "stabilizers." Thus, Baumgartner U.S. Pat. No. 2,798,096 discloses the use of a pyrophosphate as a catalyst and Barone et al U.S. Pat. No. 3,816,540 also adds certain pyrophosphates or other polyphosphates to the reaction system. Berneis U.S. Pat. No. 2,820,832 proposes the use of a copper salt or a silver salt to improve the oxidation reaction, Rovelli U.S. Pat. No. 2,897,239 employs calcium carbonate, Mead et al U.S. Pat. No. 3,647,886 uses KF, McAvoy U.S. Pat. No. 3,833,663 proposes the addition of alkali metal and alkaline earth metal fluorides, and Armstrong et al U.S. Pat. No. 3,187,055 provides for the presence in the oxidation reaction mixture of carbonates, hydroxides, oxides, and normal phosphates or ammonia. Erickson et al U.S. Pat. No. 2,867,666 uses alkali metal carbonates and alkaline earth metal carbonates or oxides but state that strong bases such as sodium hydroxide are not suitable. Aoshima et al U.S. Pat. No. 3,839,461 adds salts of certain fatty acids. Binning et al U.S. Pat. No. 2,655,545 uses transition metals such as iron, cobalt, nickel, copper, lanthanum, lead, thallium, cerium and manganese, whereas Fortuin et al U.S. Pat. No. 2,749,368 proposes the use of copper, silver and gold or their alloys.

Some prior proposals have involved the use of various alkaline agents to neutralize the acids in the system or for pH control. Such uses are exemplified by Whitfield U.S. Pat. No. 2,973,310, Armstrong et al U.S. Pat. No. 2,632,772, Dougherty U.S. Pat. No. 2,790,004 and Shiffler et al U.S. Pat. No. 2,829,173.

While these various additives knwon to the art, such as those mentioned above, apparently function to improve the reaction in one way or another when they are used in substantial quantities in the manner proposed in the art, in a system wherein the hydroperoxide is used to epoxidize an olefin to produce an oxirane compound, they introduce a serious practical complication in that they cause unacceptable precipitation of the epoxidation catalyst and concurrent substantial loss of valuable material. Moreover, some of the prior art additives introduce ions into the system which generally cannot be tolerated in the epoxidation environment.

The additives which are thus introduced into the oxidation mixture in accordance with the teachings of the prior art must, therefore, be in large measure separated prior to the use of the hydroperoxide in order to reduce as much as possible their adverse effect in reactions subsequent to the hydroperoxide-forming oxidation.

It has also been proposed to "wash" the hydrocarbon after separation from the oxidation effluent, and/or after separation from the epoxidation effluent with various alkaline solutions in order to purify the recycled hydrocarbon and in this way to improve the oxidation reaction by removing at least some of the contaminants which tend to have an adverse effect upon the oxidation. These techniques, as exemplified by Shinohara U.S. Pat. No. 3,592,857, Pell et al U.S. Pat. No. 3,439,001 and Bonnart et al U.S. Pat. No. 3,510,526, while having beneficial effects, can be somewhat erratic in their action and cause fluctuations in the oxidation, and they obviously involve additional operations which complicate the overall process, require special equipment, necessitate substantial reagent costs, and present disposal problems, much like the procedures which are necessary to separate the previously-mentioned added catalysts, inhibitors, promoters and the like, proposed by the prior art.

It is accordingly an object of the present invention to provide an improved process for the oxidation of ethylbenzene to produce ethylbenzene hydroperoxide.

It is a further object of the invention to provide a process of the character indicated which does not cause an adverse effect upon the subsequent reaction of the ethylbenzene hydroperoxide with olefins to produce oxirane compounds.

In accordance with the invention, it has been discovered that oxidation rates can be increased, selectivity to hydroperoxide can be improved, the adverse effect of contaminants can be minimized and the resultant hydroperoxide can readily be employed in an epoxidation reaction, without loss of valuable epoxidation catalysts, by having present in the hydrocarbon feed to the oxidation reaction a controlled very small amount of sodium hydroxide, potassium hydroxide or a salt of sodium or potassium. In general, the salt can be characterized as having a solubility in the reaction medium such that the small quantities referred to below will be in solubilized form. Preferably, the salt is alkaline reacting, i.e., it gives an alkaline reaction in aqueous solution. Examples of such salts are the phosphates, the carbonates, the alkanoates containing up to 20 carbon atoms, and the like. Typical salts include sodium pyrophosphate, potassium pyrophosphate, disodium phosphate, dipotassium phosphate, sodium carbonate, potassium carbonate, sodium acetate, potassium acetate, sodium neodecanoate, potassium neodecanoate, and the like. It has been discovered that a very small quantity corresponding to 0.1 to 20 ppm, preferably 0.2 to 10 ppm, and most suitably 0.5 to 2 ppm, based on hydrocarbon feed, of sodium as sodium hydroxide, or a salt of sodium, and 0.17 to 34 ppm, preferably 0.34 to 17 ppm, and most suitably 0.85 to 3.4 ppm, based on hydrocarbon feed, of potassium as potassium hydroxide or a salt of potassium are surprisingly effective in bringing about this favorable combination of desired results. What is particularly surprising is the fact that sodium or potassium compounds such as potassium hydroxides or salts have the desired beneficial effects when used in the above-mentioned quantities, whereas compounds of other alkali metals, such as lithium hydroxide or lithium phosphate, have no measurable action upon the reaction rate, hydrocarbon selectivity and the effect of contaminants. In other words, it has been discovered that a certain select few of the many additives and reagents known to the art can be effectively used to solve the important practical problems discussed above, if they are used in controlled very small quantities which are substantially lesser in magnitude than the quantities heretofore proposed. Indeed, the treament is so effective that the contaminated recycle benzene can perform better than fresh hydrocarbon (not treated in accordance with the invention) in terms of selectivity and reaction rate. It has been surprisingly discovered that the addition of sodium or potassium compounds in controlled very small quantities in accordance with the invention improves not only the performance of contaminated recycle hydrocarbon but also improves the performance of fresh or "virgin" hydrocarbon to a meaningful extent as well.

The quantity of the sodium or potassium compound to be used can be incorporated in the feed in any desired manner but it has been found that optimum control of the small concentration of the sodium or potassium compound is most effectively achieved by adding the desired quantity to the oxidizer feed. Depending upon the volume of the hydrocarbon being handled, the sodium or potassium compound can be added as a solid preferably finely divided to insure uniform distribution when the hydrocarbon is agitated, or it may be added as an aqueous solution. The latter method of addition is preferred to insure the desired control of the concentration at the selected low value.

While the process of this invention is not limited to any particular oxidation procedure for the production of hydroperoxides using molecular oxygen, i.e., so-called "auto oxidation," the oxidation can be effected in any standard equipment suitable for oxidation reactions, and the oxidation can be carried out batch-wise or continuously with equal facility, the formation of the hydroperoxides is normally brought about within certain parameters of temperature, pressure and the like and the invention will be more easily understood by describing it in connection with typical operating conditions and with respect to typical reactants and material handling procedures.

For example, any oxygen-bearing gas may be used in this process providing that the gases other than oxygen are inert at the reaction conditions. Air is the preferred oxidation gas because of its ready availability but gases richer or poorer in oxygen than air may be used.

The amount of hydrocarbon that should be converted in any oxidation depends upon several competing factors. As the conversion is increased above 20% of the feed hydrocarbon, the amount of by-product increases rapidly and the yield of hydroperoxide is consequently decreased. When the conversion is less than about 5%, the cost of oxidizing a unit amount of hydrocarbon is greatly increased due to the requirements of additional hydrocarbon recycle.

The temperatures at which the hydrocaron is oxidized are about 125° to 165° C., the preferred range is about 130° to 160° C., and it is most desirable to operate in the range of about 135° to 160° C. At temperatures lower than 125° C., the rate of reaction is undesirably low and temperatures in excess of 165° C. have an adverse effect upon selectivity. Advantageously, the oxidation reaction is performed under programmed temperature conditions rather than at one temperature. The formation of by-products can be minimized if the temperature of the oxidation is maintained at an initially high value and then decreased during the course of the oxidation. Although temperature programming of the reaction requires careful process control, the overall advantages accruing to the process because of reduced reaction times or smaller by-product formation are more than substantial. Thus, during about one half of the total reaction time required to convert the desired percentage of hydrocarbon, the temperature should be controlled in the range of about 135° to 165° C. During the remainder of the total reaction time the reaction temperature should be maintained between about 125° C. and about 155° C. It is important that the temperature during the second half of the reaction be lower than the temperature during the first half of the reaction. It is, of course, possible to reduce the reaction temperature according to any desired rate. It is only of importance that the average temperature during the later part of the reaction be less than the reaction temperaure during the earlier part of the reaction. By accelerating the rate of reaction of hydroperoxide during the early part of the reaction, the concentrated hydroperoxide solution is maintained at high process temperatures for a shorter period, thereby decreasing or at least maintaining constant the amount of by-product formation.

The reaction pressure may be maintained at from about atmospheric to 1000 p.s.i.g., although the pressure is desirably maintained at from 10 p.s.i.g. to 200 p.s.i.g. The oxidation of hydrocarbons is exothermic and it is, of course, necessary that some heat be removed. It is, therefore, most desirable to operate at the adiabatic pressure, that is the pressure at which all of the excess heat produced in the reaction is removed as latent heat of vaporization in boiled-up hydrocarbon since there is then no requirement for cooling coils or water-jacketed reaction vessels or other types of heat-removal apparatus, nor is there any net heat reuirement once the reaction mixture has been brought to temperature and initiated. The adiabatic pressure depends upon the temperature of the reaction, the amount of feed gas, the reactant feed temperature, the degree of hydrocarbon conversion, etc., and thus cannot be specifically defined except in relation to these variables. When operating at this pressure, all of the heat of reaction is removed in an overhead vent condenser wherein the boiled up hydrocarbon is condensed and returned to the reaction vessel.

The time required to convert the desired quantity of the hydrocarbon is in the range of from 1/2 to 20 hours depending upon the temperature maintained in the reactor and the oxygen partial pressure.

The above-described oxidation results in an oxidation mixture containing unconverted hydrocarbon and reaction products, predominantly the hydroperoxide along with by-products or co-products such as ketones, alcohols, aldehydes, acids and water. Advantageously, the water is removed, e.g., by decantation. It is possible to use the oxidate formed in accordance with the process of this invention without further purification in the epoxidation of an olefinic compound but it is generally desirable to remove at least some, and preferably the major portion of the unconverted hydrocarbons prior to the epoxidation step. This is readily effected by distillation. When operating in this fashion, less epoxidation reactor volume is required. The hydrocarbon present can be removed in conventional manner, e.g., by distillation, following the epoxidation reaction for recycling to the oxidation step.

The epoxidation using the thus-produced ethylbenzene hydroperoxide is advantageously carried out in the presence of epoxidation catalysts which may be compounds of Ti, V, Se, Cr, Zr, Nb, Ta, Te, U, Mo, W and Re. The preferred catalysts are compounds of Mo, Ti, V, W, Re, Se, Nb and Te.

The amount of metal in solution used as catalyst in the epoxidation process can be varied widely, although as a rule it is desirable to use at least 0.00001 mol and preferably 0.002 to 0.03 mol per mol of hydroperoxide present, but amounts up to 1 mol or more per mol of hydroperoxide can be employed. The catalysts remain dissolved in the reaction mixture and can be reused in the reaction after removal of the reaction products therefrom. The molybdenum compounds include the molybdenum organic salts, the oxides such as $Mo_3O_3$, $MoO_3$, molybdic acid, the molybdenum chlorides and oxychlorides, molybdenum fluoride, phosphate, sulfide, and the like. Hetero-polyacids containing molybdenum can be used as can their salts. Examples include phosphomolybdic acid and the sodium and potassium salts thereof. Similar or analagous compounds of the other metals mentioned may be used, as may their mixtures.

The catalytic components may be employed in the epoxidation reaction in the form of a compound or mixture which is initially soluble in the reaction medium. Illustrative soluble forms of the catalytic materials are the naphthenates, stearates, octoates, carbonyls and the like. Various chelates, association compounds and enol salts, such for example, as aceto-acetonates may also be used. Specific and preferred catalytic compounds of this type for use in the invention are the naphthenates and carbonyls of molybdenum, vanadium, titanium, tungsten, rhenium, tantalum and selenium. Alkoxy compounds such as tetrabutyl titanate and other like alkyl titanates are very useful.

Temperatures which can be employed in the epoxidation can vary quite widely depending upon the reactivity and other characteristics of the particular system. Temperatures broadly in the range of about −20° to 200° C., desirably 0° to 150° C., and preferably 50° C. to 120° C. can be employed. The reaction is carried out at pressure conditons sufficient to maintain a liquid phase. Although sub-atmospheric pressures can be employed, pressures usually in the range of about atmoshperic to about 1000 p.s.i.g. are most desirable.

Olefinically unsaturated materials which can be epoxidized by the hydroperoxide include substituted and unsubstituted aliphatic and alicyclic olefins which may be hydrocarbons or esters or alcohols or ketones or ethers or the like. Preferred compounds are those having from about 2 to 30 carbon atoms and preferably at least 3 carbon atoms. Illustrative olefins are ethylene, propylene, normal butylene, isobutylene, the pentenes, the methyl pentenes, the normal hexenes, the octenes, the dodecenes, cyclohexene, methyl cyclohexene, butadiene, styrene, methyl styrene, vinyl toluene, vinyl cyclohexene, the phenyl cyclohexenes, and the like. Olefins having halogen, oxygen, sulfur and the like containing substituents can be used. Such substituted olefins are illustrated by allyl alcohol, methallyl alcohol, cyclohexanol, diallyl ether, methyl methacrylate, methyl oleate, methyl vinyl ketone, allyl chloride, and the like. In general, all olefinic materials epoxidized by methods previously employed can be epoxidized in accordance with this process including olefinically-unsaturated polymers.

The lower olefins having about 3 or 4 carbon atoms in an aliphatic chain are most advantageously epoxidized by the reaction with the hydroperoxide, e.g. ethylbenzene hydroperoxide. The class of olefins commonly termed alpha-olefins or primary olefins are also epoxidized in a particularly efficient manner by this process. It is known to the art that these primary olefins, e.g., propylene, butene-1, decene-1, hexadecene-1, etc., are epoxidized with more difficulty than other forms of olefins, except for ethylene. Other forms of olefins which are more easily epoxidized are substituted olefins, alkenes with internal unsaturation, cycloalkenes, and the like.

In the epoxidation, the ratio of olefin to hydroperoxide can vary over a wide range. Generally, mol ratios of olefinic groups to hydroperoxide broadly in the range of 0.5:1 to 100:1, desirably 1:1 to 20:1 and preferably 2:1 to 10:1 are employed. Additionally, it is advantageous to carry out the reaction to achieve as high a hydroperoxide conversion as possible, preferably at least 50% and desirably at least 90%, consistent with reasonable selectivities.

The following examples illustrate the invention in more specific detail and demonstrate the effect of the controlled addition of very small quantities of sodium or potassium compounds in the oxidation of hydrocarbons to produce ethylbenzene hydroperoxide in accordance with the process of the invention. The apparatus used in each case was a glass 500 ml. resin kettle provided with a glass "vibro-mix" agitator, an air-supply conduit into which air and/or nitrogen could be introduced, a sample-withdrawal line, a thermometer and a reflux condenser, connected to a pressure-controlled vent line. The oxygen concentration was measured in the off-gas continuously to maintain the desired oxygen partial pressure in the system. Liquid-phase temperature was controlled by a "thermowatch" using a conventional heating mantle.

Between each of the runs to which sodium or potassium compounds were added, the system was washed with ethylbenzene, dried and then filled with 40% nitric acid, heated to 60°–70° C. for one hour, drained, and washed 6-7 times with distilled water. No detectable acid titer was observed in the final wash when the entire wash was titered. The system was then dried and flushed with ethylbenzene prior to charging reactants.

In the oxidations described below, the "recycle" feed consisted of ethylbenzene obtained from prior oxidates after conventional processing to concentrate the ethylbenzene hydroperoxide by removing a portion of the ethylbenzene (about 50%) followed by epoxidation of propylene using the concentrated hydroperoxide and conventional distillation to remove the remaining ethylbenzene, the ethylbenzene recycle streams being combined with make-up ethylbenzene in a volume ratio of about 85 parts recycle to 15 parts make-up. This mixture will be referred to a recycle ethylbenzene below.

EXAMPLE 1

Comparative oxidations were carried out using the apparatus and procedure described above. The experiments were made with 100% virgin ethylbenzene as feed and with recycle ethylbenzene feed. The reaction was effected at 140° C. with an oxygen partial pressure of 0.3–0.6 psi. The following table shows the data for these oxidations:

| WEIGHT % EBHP IN EFFLUENT | EBHP SELECTIVITY (MOLAR %) | | |
|---|---|---|---|
| | Virgin | Recycle | Difference |
| 8 | 89.2 | 86.7 | −2.5 |
| 10 | 86.7 | 83.9 | −2.8 |
| 12 | 83.7 | 80.3 | −3.4 |
| 13.5 | 81.0 | 77.0 | −4.0 |
| 15 | 78.1 | 73.0 | −5.1 |
| 16 | 76.0 | 68.3 | −7.7 |

As can be seen from the above data, recycle ethylbenzene resulted in a lower selectivity than virgin ethylbenzene, the difference increasing with conversion.

EXAMPLE 2

A series of runs were carried out in which sodium as sodium pyrophosphate (SPP) was added to virgin ethylbenzene at a level of 1.0 ppm. The following comparative results were obtained:

| WEIGHT % EBHP IN EFFLUENT | EBHP SELECTIVITY (MOLAR %) | | |
|---|---|---|---|
| | Virgin | Virgin + SPP | Difference |
| 8 | 89.2 | 90.5 | +1.3 |
| 10 | 86.7 | 88.8 | +2.1 |
| 12 | 83.7 | 86.8 | +3.1 |
| 13.5 | 81.0 | 85.0 | +4.0 |
| 15 | 78.1 | 83.0 | +4.9 |
| 16 | 76.0 | 81.6 | +5.6 |

The improvement as a result of adding the pyrophosphate is apparent. It is to be noted that the acidity in the effluent at the 16% EBHP level is about 15 meq/kg. The level of 1 ppm sodium as SPP corresponds to a basic level of 0.04 meq/kg. Obviously, this level of sodium is not serving the role of neutralizing acidity.

EXAMPLE 3

A series of runs were made in which sodium as sodium pyrophosphate was introduced to recycle ethylbenzene at a level of 1.0 ppm. The following comparative results were obtained:

| WEIGHT % EBHP | EBHP SELECTIVITY (MOLAR %) | | |
|---|---|---|---|
| IN EFFLUENT | Recycle EB | Recycle + SPP | Difference |
| 8 | 86.7 | 90.5 | +3.8 |
| 10 | 83.9 | 88.8 | +4.9 |
| 12 | 80.1 | 86.8 | +6.5 |
| 13.5 | 77.0 | 85.0 | +8.0 |
| 15 | 23.0 | 83.0 | +10.0 |
| 16 | 68.3 | 81.6 | +13.3 |

The results using recycle ethylbenzene with SPP are equivalent to those obtained with virgin ethylbenzene and SPP and, of course, significantly better than the data obtained when using recycle ethylbenzene without additive.

EXAMPLE 4

Recycle ethylbenzene was oxidized with different levels of sodium as SPP, namely 0.2, 1.0, 10.0, and 20.0 ppm. No difference in the selectivity or rate was observed from the data described in Example 3.

EXAMPLE 5

A comparison was made of the relative rates of EBHP formation as a function of the type of feed used with and without the addition of SPP. The following results were obtained:

| Feed | Rate (Wt. % EBHP Formed/Hr.) |
|---|---|
| Virgin EB | 2.9 |
| Virgin EB + 1.0 ppm sodium as SPP | 3.5 |
| Recycle EB | 2.9 |
| Recycle EB + 1.0 ppm sodium as SPP | 3.6 |

There is a significant improvement in the rate of hydroperoxide formation when using the SPP.

EXAMPLE 6

A study was made to determine the relative rates of reaction when using 0.2, 1.0, 10.0, and 20.0 ppm of sodium as SPP in recycle EB. The results of these tests showed that the rates at all three levels were similar to those described in Example 5.

EXAMPLE 7

In order to be certain that the rate of reaction was not limited by mass transfer characteristics of the system, several different temperatures were studied. The following rates were observed using recycle EB with 1.0 ppm of sodium as SPP.

| Rate (% EBHP/Hr.) | Temp. °C. |
|---|---|
| 3.6 | 140 |
| 1.8 | 130 |

These results indicate that the reaction is typically first order and the previously reported rate improvements were a result of the presence of the SPP.

EXAMPLE 8

A series of tests were made to determine the effect of SPP when it was used to passivate the walls of the glass vessel. The vessel was filled with a 3% solution of SPP at 80° C. Agitation was maintained for 30 minutes, the system drained, and then dried with nitrogen, leaving a film of SPP on the walls. A series of runs were made with recycle ethylbenzene. Between runs, the system was not cleaned. The following results were obtained:

| | | Change in Selectivity (Molar percentage points) | Rate (% EBHP/HR.) |
|---|---|---|---|
| Cycle | 1 | 0 | 3.6 |
| | 2 | −0.7 | 3.2 |
| | 3 | −5.1 | 3.0 |
| | 4 | −6.1 | 2.9 |

It is apparent that as the SPP dissolves in the oxidate, the rate and selectivity of subsequent runs deteriorates until the fourth cycle where the data are comparable to results obtained with recycle ethylbenzene containing no SPP.

EXAMPLE 9

To determine the effect of SPP on the rate of epoxidation, the oxidates made in Example 4 were used as feed for propylene epoxidation in the presence of a molybdenum catalyst. The relative rates of epoxidation were observed as follows:

| Level of Sodium as SPP in Oxidate | EBHP Conversion After 60 Min. Epoxidation (130° C. 20 ppm, Catalyst as Mo.) |
|---|---|
| 0 | 98.5 |
| 0.2 | 98.3 |
| 0.5 | 99.0 |
| 1.0 | 99.3 |
| 10.0 | 85.2 |
| 20.0 | 15.3 |

It is clear that at levels above 20 ppm., the bulk of the molybdenum catalyst in the epoxidation was precipitated by the sodium.

EXAMPLE 10

A series of runs were made in which 1.7 ppm. of potassium as potassium pyrophosphate were added to recycle ethylbenzene. Results comparable to Examples 3 and 5 were obtained.

EXAMPLE 11

A series of runs were made in which 1.0 ppm of sodium as NaOH was added to recycle ethylbenzene. Results comparable to Examples 3 and 5 were obtained.

EXAMPLE 12

A series of runs were made in which 1.0 ppm. of sodium as disodium phosphate, sodium acetate, and sodium neodecanoate were added separately. Results comparable to Examples 3 and 5 were obtained.

I claim:

1. A process for the preparation of ethylbenzene hydroperoxide which comprises oxidizing ethylbenzene with molecular oxygen at a temperature of 125° to 165° C. at a pressure of from about atmospheric to 1,000 psig, the ethylbenzene being oxidized having added to it a controlled amount of a hydroxide or salt of sodium or potassium in the amount of 0.1 to 20 parts per million of sodium or 0.17 to 34 parts per million of potassium so that said hydroxide or salt is present during the oxidation of said ethylbenzene whereby to increase the reaction rate of said oxidation and to increase the selectivity of said oxidation to the ethylbenzene hydroperoxide and to produce a hydroperoxide reaction mixture characterized by a composition which when used directly, or after removal of at least some of the unreacted ethylbenzene, in the catalytic epoxidation of olefins in the presence of an epoxidation catalyst which is a compound of Ti, V, Se, Cr, Zr, Nb, Ta, Te, U, Mo, W or Re in the amount of at least 0.00001 up to 1 mol per mol of hydroperoxide at a temperature in the range of about −20° C. to 200° C. under pressure conditions sufficient to maintain a liquid phase will not cause undue precipitation of epoxidation catalyst with concurrent reduction in the reaction rate of the epoxidation.

2. A process as defined in claim 1, wherein the amount of sodium is 0.2 to 10 parts per million and the amount of potassium is 0.34 to 17 parts per million.

3. A process as defined in claim 1, wherein the amount of sodium is 0.5 to 2 parts per million and the amount of potassium is 0.85 to 3.4 parts per million.

4. A process as defined in claim 1, wherein a hydroxide of sodium or potassium is added to the ethylbenzene.

5. A process as defined in claim 1, wherein a salt of sodium or potassium is added to the ethylbenzene.

6. A process as defined in claim 1, wherein the ethylbenzene being oxidized comprises recycle ethylbenzene from a previous oxidation.

7. A process as defined in claim 1, wherein the ethylbenzene being oxidized comprises recycle ethylbenzene from a previous oxidation.

8. A process as defined in claim 1, wherein said amount is less than 50% of the amount required to neutralize the acidity.

9. The process which comprises oxidizing ethylbenzene with molecular oxygen at a temperature of 125°–165° C. and at a pressure of from about atmospheric to 1,000 psig in an oxidizing zone to produce a hydroperoxide corresponding to said ethylbenzene while adding to the ethylbenzene being oxidized a controlled amount of a hydroxide or salt of sodium or potassium in the amount of 0.1 to 20 parts per million of potassium so that said hydroxide or salt is present during the oxidation of said ethylbenzene whereby to increase the reaction rate of said oxidation and to increase the selectivity of said oxidation to the hydroperoxide removing said hydroperoxide from said oxidation zone and directly, or after removal of at least some of the unreacted ethylbenzene, reacting said hydroperoxide with an olefin in the presence of an epoxidation catalyst which is a compound of Ti, V, Se, Cr, Zr, Nb, Ta, Te, U, Mo, W or Re in the amount of at least 0.00001 up to 1 mol per mol of hydroperoxide at a temperature in the the range of about −20° C. to 200° C. under pressure conditions sufficient to maintain a liquid phase to form the epoxide of said olefin without causing undue precipitation of epoxidation catalyst with concurrent reduction in reaction rate of the epoxidation reaction.

10. The process as defined in claim 9, wherein the amount of sodium is 0.2 to 10 parts per million and the amount of potassium is 0.34 to 17 parts per million.

11. The process as defined in claim 9, wherein the amount of sodium is 0.5 to 2 parts per million and the amount of potassium is 0.85 to 3.4 parts per million.

12. A process for the preparation of ethylbenzene hydroperoxide which comprises oxidizing ethylbenzene with molecular oxygen at a temperature of 125° to 165° C. at a pressure of from about atmospheric to 1,000 psig, the ethylbenzene being oxidized having added to it a controlled amount of a hydroxide or salt of sodium or potassium in the amount of 0.1 to 20 parts per million of sodium or 0.17 to 34 parts per million of potassium so that said hydroxide or salt is present during the oxidation of said ethylbenzene whereby to increase the reaction rate of said oxidation and to increase the selectivity of said oxidation to the ethylbenzene hydroperoxide and to produce a hydroperoxide reaction mixture characterized by a composition which when used directly, or after removal of at least some of the unreacted ethylbenzene, in the catalytic epoxidation of propylene in the presence of an epoxidation catalyst which is a compound of Ti, V, Se, Cr, Zr, Nb, Ta, Te, U, Mo, W or Re in the amount of at least 0.00001 up to 1 mol of hydroperoxide at a temperature in the range of about −20° C. to 200° C. under pressure conditions sufficient to maintain a liquid phase will not cause undue precipitation of epoxidation catalyst with concurrent reduction in the reaction rate of the epoxidation, the amount of said hydroxide or salt of sodium or potassium being less than that required to neutralize the acidity of the reaction mixture of said oxidation.

13. A process as defined in claim 12, wherein the amount of sodium is 0.2 to 10 parts per million and the amount of potassium is 0.34 to 17 parts per million.

14. A process for the preparation of ethylbenzene hydroperoxide which comprises oxidizing ethylbenzene with molecular oxygen at a temperature of 125° to 165° C. at a pressure of from about atmospheric to 1,000 psig, the ethylbenzene being oxidized having added to it a controlled amount of a hydroxide or salt of sodium or potassium in the amount of 0.1 to 20 parts per million of sodium or 0.17 to 34 parts per million of potassium so that said hydroxide or salt is present during the oxidation of said ethylbenzene, whereby to increase the reaction rate of said oxidation and to increase the selectivity of said oxidation to the ethylbenzene hydroperoxide and to produce a hydroperoxide reaction mixture characterized by a composition which when used directly, or after removal of at least some of the unreacted ethylbenzene, in the catalytic epoxidation of olefins in the presence of an epoxidation catalyst which is a compound of molybdenum in the amount of at least 0.00001 up to 1 mol per mol of hydroperoxide at a temperature in the range of about −20° C. to 200° C. under pressure conditions sufficient to maintain a liquid phase will not cause undue precipitation of molybdenum epoxidation catalyst with concurrent reduction in reaction rate of the epoxidation, the amount of said hydroxide or salt of sodium or potassium being less than that required to neutralize the acidity of the reaction mixture of said oxidation.

15. A process as defined in claim 14, wherein the amount of sodium is 0.5 to 2 parts per million and the amount of potassium is 0.85 to 3.4 parts per million.

16. The process which comprises oxidizing ethylbenzene with molecular oxygen at a temperature of 125° to 165° C. and at a pressure of from about atmospheric to 1,000 psig in an oxidizing zone to produce a hydroperoxide corresponding to said ethylbenzene while adding to the ethylbenzene being oxidized a controlled amount of a hydroxide or salt of sodium or potassium in the amount of 0.1 to 20 parts per million of sodium or 0.17 to 34 parts per million of potassium so that said hydroxide or salt is present during the oxidation of said ethylbenzene whereby to increase the reaction rate of said oxidation and to increase the selectivity of said oxidation to the hydroperoxide, removing said hydroperoxide from said oxidation zone and directly, or after removal of at least some of the unreacted ethylbenzene, reacting said hydroperoxide and propylene in the presence of a molybdenum catalyst in the amount of at least 0.00001 up to 1 mol per mol of hydroperoxide at a temperature in the range of about −20° C. to 200° C. under pressure conditions sufficient to maintain a liquid phase to form propylene oxide without causing undue precipitation of the molybdenum catalyst with concurrent reduction in the reaction rate of the epoxidation reaction.

* * * * *